United States Patent
Bhalla et al.

(10) Patent No.: US 11,026,676 B2
(45) Date of Patent: Jun. 8, 2021

(54) SURGICAL WOUND CLOSURE APPARATUS

(71) Applicant: Covidien LP, Mansfield, MA (US)

(72) Inventors: Inderjeet Singh Bhalla, Telangana (IN); Neeraj Kumar, Uttar Pradesh (IN)

(73) Assignee: Covidien LP, Mansfield, MA (US)

( * ) Notice: Subject to any disclaimer, the term of this patent is extended or adjusted under 35 U.S.C. 154(b) by 567 days.

(21) Appl. No.: 15/863,025

(22) Filed: Jan. 5, 2018

(65) Prior Publication Data

US 2018/0221015 A1    Aug. 9, 2018

Related U.S. Application Data

(60) Provisional application No. 62/455,077, filed on Feb. 6, 2017.

(51) Int. Cl.
*A61B 17/04* (2006.01)
*A61B 17/06* (2006.01)

(52) U.S. Cl.
CPC ...... *A61B 17/0482* (2013.01); *A61B 17/0469* (2013.01); *A61B 17/06066* (2013.01); *A61B 2017/047* (2013.01); *A61B 2017/0608* (2013.01)

(58) Field of Classification Search
CPC ............ A61B 17/0469; A61B 17/0482; A61B 17/062; A61B 2017/0491; A61B 2017/06076; A61B 2017/0608; A61B 2017/047

See application file for complete search history.

(56) References Cited

U.S. PATENT DOCUMENTS

| 3,807,407 A | * | 4/1974 | Schweizer | A61B 17/04 606/145 |
| 4,935,027 A | * | 6/1990 | Yoon | A61B 17/0469 606/146 |
| 5,364,408 A | * | 11/1994 | Gordon | A61B 17/0469 606/144 |
| 5,368,601 A | | 11/1994 | Sauer et al. | |

(Continued)

OTHER PUBLICATIONS

Partial European Search Report dated Mar. 21, 2018 issued in EP Application No. 18155156.

(Continued)

*Primary Examiner* — Dianne Dornbusch

(57) ABSTRACT

A surgical closure apparatus for facilitating closure of a wound includes an outer member dimensioned for positioning within a wound opening and defining a central longitudinal axis, and having a first longitudinal passage and a second longitudinal passage, a needle assembly at least partially disposed within the first longitudinal passage of the outer member, and a suture configured for at least partially closing the wound opening and extending at least partially through the second longitudinal passage of the outer member. The needle assembly includes a needle drive and a suture needle mounted to the needle drive and coupled to the suture. The suture needle is adapted for rotational movement relative to the central longitudinal axis between an unarmed condition and an armed condition through manipulation of the needle drive. The suture needle is positioned for passage through tissue adjacent the wound opening when in the armed condition.

9 Claims, 8 Drawing Sheets

(56) References Cited

U.S. PATENT DOCUMENTS

| | | | | |
|---|---|---|---|---|
| 5,374,275 A * | 12/1994 | Bradley | ............ | A61B 17/0469 606/139 |
| 5,527,321 A * | 6/1996 | Hinchliffe | .......... | A61B 17/0469 112/169 |
| 5,540,705 A * | 7/1996 | Meade | ............... | A61B 17/0491 606/139 |
| 5,573,540 A * | 11/1996 | Yoon | ................. | A61B 17/0469 606/139 |
| 5,814,065 A * | 9/1998 | Diaz | ................. | A61B 17/0469 112/169 |
| 5,957,937 A * | 9/1999 | Yoon | ................. | A61B 17/0469 606/144 |
| 5,972,005 A * | 10/1999 | Stalker | ............... | A61B 17/0057 606/144 |
| 5,984,932 A * | 11/1999 | Yoon | ................. | A61B 17/0469 606/147 |
| 6,071,289 A * | 6/2000 | Stefanchik | ......... | A61B 17/0469 606/144 |
| 6,086,601 A * | 7/2000 | Yoon | .................... | A61B 17/062 606/139 |
| 6,136,010 A * | 10/2000 | Modesitt | ............ | A61B 17/0057 606/139 |
| 6,358,258 B1 * | 3/2002 | Arcia | ................. | A61B 17/0469 606/139 |
| 7,449,024 B2 * | 11/2008 | Stafford | ............. | A61B 17/0469 606/144 |
| 8,465,506 B2 * | 6/2013 | McLawhorn | ...... | A61B 17/0625 606/145 |
| 2002/0173800 A1 * | 11/2002 | Dreyfuss | ............ | A61B 17/0625 606/139 |
| 2005/0043589 A1 * | 2/2005 | Pruitt | ................. | A61B 1/00101 600/176 |
| 2007/0213757 A1 | 9/2007 | Boraiah | | |
| 2008/0132943 A1 | 6/2008 | Maiorino et al. | | |
| 2008/0249543 A1 * | 10/2008 | Kaladelfos | ......... | A61B 17/0625 606/144 |
| 2008/0277450 A1 * | 11/2008 | Dudai | .................... | A61B 17/04 227/179.1 |
| 2009/0240264 A1 * | 9/2009 | Tuval | ................. | A61B 17/0469 606/148 |
| 2009/0264925 A1 | 10/2009 | Hotter et al. | | |
| 2010/0042144 A1 | 2/2010 | Bennett | | |
| 2010/0298866 A1 | 11/2010 | Fischvogt | | |
| 2011/0082473 A1 | 4/2011 | Smith | | |
| 2011/0082475 A1 | 4/2011 | Smith | | |
| 2011/0082477 A1 | 4/2011 | Smith | | |
| 2011/0082480 A1 | 4/2011 | Viola | | |
| 2011/0087271 A1 | 4/2011 | Sargeant et al. | | |
| 2011/0087272 A1 | 4/2011 | Sargeant et al. | | |
| 2011/0112555 A1 * | 5/2011 | Overes | ............... | A61B 17/0491 606/145 |
| 2011/0196420 A1 | 8/2011 | Ebner | | |
| 2012/0029532 A1 | 2/2012 | Hodgkinson et al. | | |
| 2012/0116445 A1 | 5/2012 | Rideout | | |
| 2012/0172926 A1 | 7/2012 | Hotter | | |
| 2012/0191132 A1 | 7/2012 | Sargeant | | |
| 2013/0197572 A1 | 8/2013 | Cohen et al. | | |
| 2013/0197573 A1 | 8/2013 | Cohen et al. | | |
| 2013/0267966 A1 | 10/2013 | Fortson et al. | | |
| 2015/0038995 A1 | 2/2015 | Malkowski | | |
| 2015/0039025 A1 | 2/2015 | Prior et al. | | |

OTHER PUBLICATIONS

European Search Report dated Jun. 25, 2018 in EP Appln. No. 18155156.

* cited by examiner

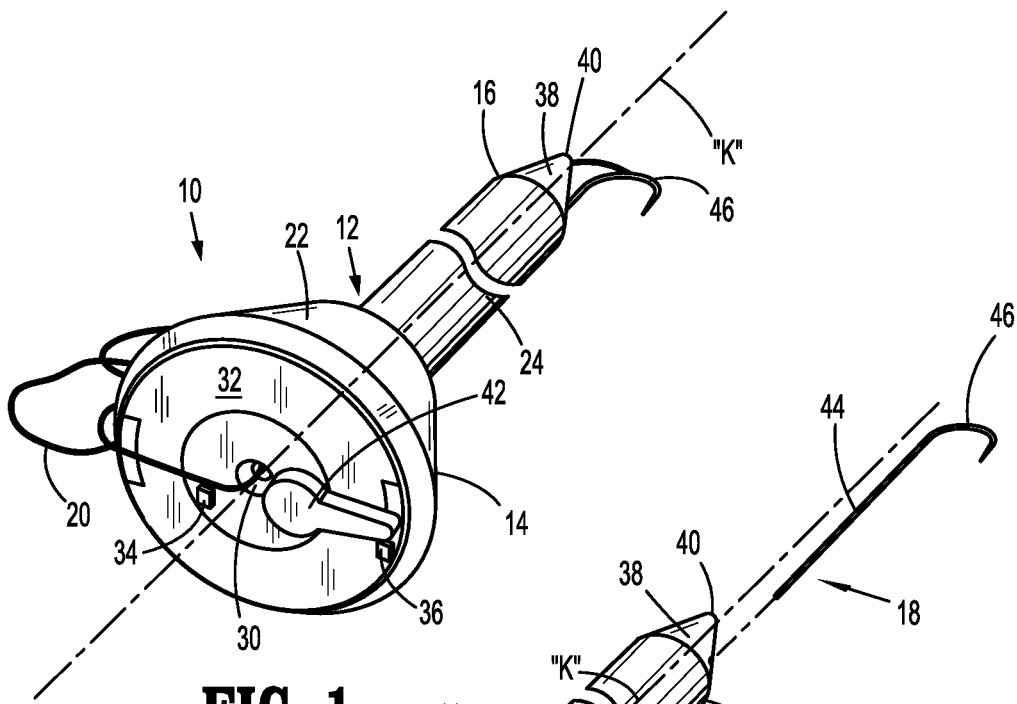
FIG. 1
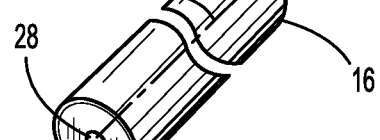
FIG. 2
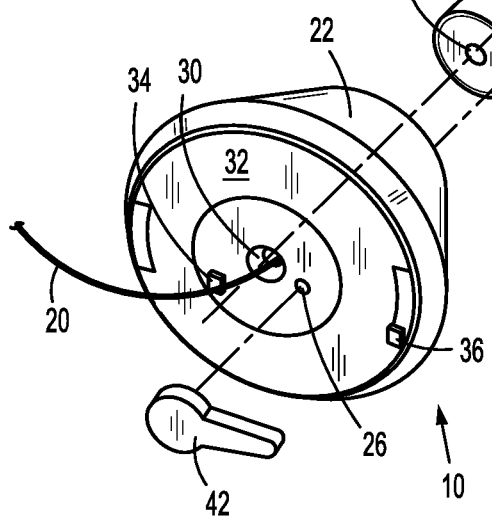
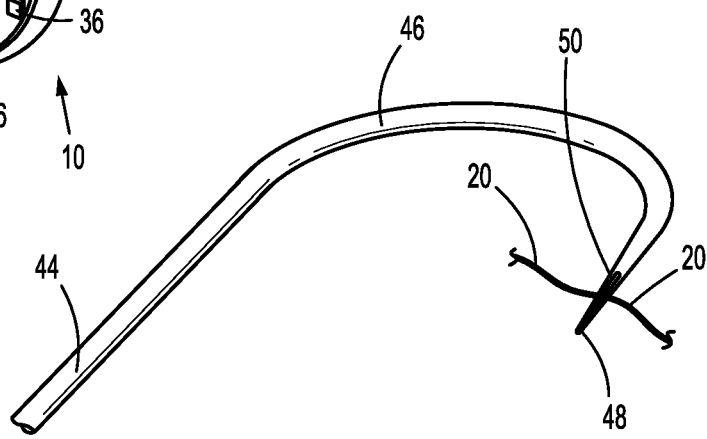
FIG. 2A

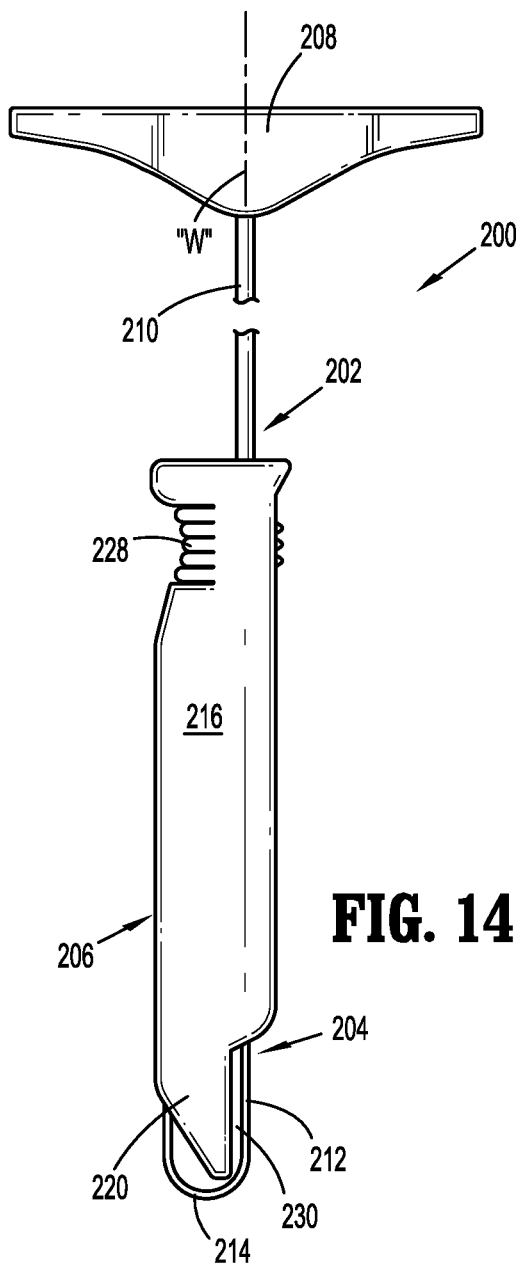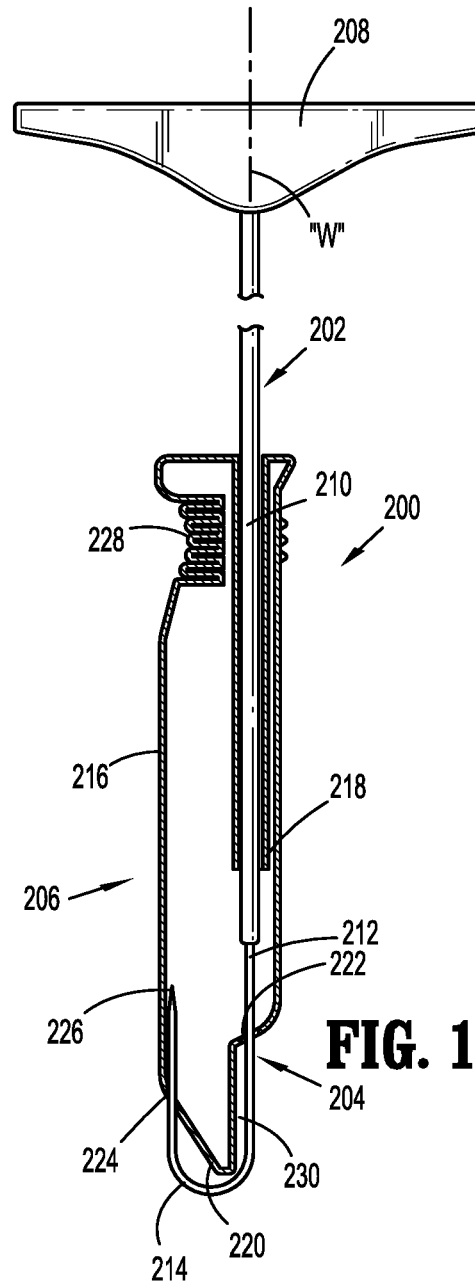

SURGICAL WOUND CLOSURE APPARATUS

CROSS-REFERENCE TO RELATED APPLICATIONS

This application claims the benefit of and priority to U.S. Provisional Patent Application No. 62/455,077 filed Feb. 6, 2017, the entire disclosure of which is incorporated by reference herein.

BACKGROUND

1. Technical Field

The present disclosure relates to wound closure and, more particularly, relates to an apparatus and associated method for closing a wound or port opening in the abdomen in conjunction with a laparoscopic surgical procedure.

2. Background of Related Art

Puncture wounds may result from trauma or may be intentionally created to provide access to a body cavity during a surgical procedure. In an endoscopic or laparoscopic surgical procedure, for example, a trocar is utilized to puncture the abdomen to provide access by way of a cannula through the abdominal wall. Generally, the cannula or other access portal device is placed through the abdominal wall for introduction of surgical instrumentation required to perform the surgical procedure. Once the procedure is complete, it is necessary to close the puncture wound.

Current methods of wound closure are highly skill dependent as advancing a needle into a small port and ensuring that the needle crosses through different layers of abdominal tissue, including subcutaneous tissue, fascia and muscle, is quite cumbersome and difficult. In addition, there is a potential of the needle inadvertently contacting and injuring organs within the abdominal cavity.

SUMMARY

Accordingly, the present disclosure is directed to further improvements in wound closure. In one embodiment, a surgical closure apparatus for facilitating closure of a wound includes an outer member dimensioned for positioning within a wound opening and defining a central longitudinal axis, and having a first longitudinal passage and a second longitudinal passage, a needle assembly at least partially disposed within the first longitudinal passage of the outer member, and a suture configured for at least partially closing the wound opening and extending at least partially through the second longitudinal passage of the outer member. The needle assembly includes a needle drive and a suture needle mounted to the needle drive and coupled to the suture. The suture needle is adapted for rotational movement relative to the central longitudinal axis between an unarmed condition and an armed condition through manipulation of the needle drive. The suture needle is positioned for passage through tissue adjacent the wound opening when in the armed condition.

The suture needle may be curved and define a needlepoint. In embodiments, at least the needlepoint of the suture needle is disposed radially outward relative to the outer member when in the armed condition of the suture needle and is disposed radially inward relative to the outer member when in the unarmed condition of the suture needle. In some embodiments, the needle drive is rotatable within the first longitudinal passage of the outer member to cause corresponding rotational movement of the suture needle between the unarmed condition and the armed condition. In embodiments, the needle assembly includes a manual actuator coupled to the needle drive and movable to cause corresponding rotational movement of the needle drive and the suture needle between the unarmed condition and the armed condition.

In some embodiments, the outer member includes a housing and an elongate member extending from the housing. The manual actuator is mounted to the housing for rotational movement between a first position corresponding to the unarmed condition of the suture needle and a second position corresponding to the armed condition of the suture needle. In embodiments, the housing includes a first stop for engaging the manual actuator at the first position and a second stop for engaging the manual actuator at the second position.

The outer member may include a tapered end segment configured to facilitate passage through the wound opening.

In an embodiment, a surgical closure apparatus for facilitating closure of a wound includes an elongate member dimensioned for positioning within a wound opening and defining a central longitudinal axis, a protective ledge depending radially outwardly from a wall of the elongate member and a needle assembly mounted to the elongate member. The needle assembly includes a needle drive and a suture needle mounted to the needle drive. The suture needle is adapted for rotational movement through manipulation of the needle drive relative to the central longitudinal axis between an unarmed condition where the suture needle is aligned with the protective ledge and an armed condition where the suture needle is positioned for passage through the tissue adjacent the wound opening. In embodiments, a suture is coupled to the suture needle and is configured for at least partially closing the wound opening within the tissue.

A method for facilitating closure of a wound opening is also disclosed. The method includes:

positioning an outer member within a wound opening;

maneuvering a needle assembly at least partially extending within a first longitudinal passage of the outer member to move a curved needle of the needle assembly from an unarmed condition to an armed condition whereby the curved needle is disposed radially outward of the outer member, the curved needle having a suture coupled thereto;

moving the outer member within the wound opening through a first manipulation such that the curved needle penetrates first tissue portions surrounding the wound opening to cause a first suture segment of the suture to pass through the first tissue portions;

rearranging the outer member within the wound opening;

moving the outer member within the wound opening through a second manipulation such that the curved needle penetrates second tissue portions surrounding the wound opening to cause a second suture segment of the suture to pass through the second tissue portions; and securing the first and second suture segments to at least partially close the wound opening.

In embodiments, maneuvering the needle assembly includes rotating a needle drive of the needle assembly within the first longitudinal passage to cause corresponding rotational movement of the curved needle from the unarmed condition to the armed condition. In embodiments, the needle assembly includes a manual actuator coupled to the needle drive and wherein maneuvering the needle assembly includes manually rotating the manual actuator from a first position corresponding to the unarmed condition of the curved needle to a second position corresponding to the armed condition of the curved needle.

In some embodiments, the outer member has a second longitudinal passage for accommodating the suture and wherein, during moving the outer member through each of the first and second manipulations, the suture slides within the second longitudinal passage. In embodiments, moving the outer member within the wound opening through each of the first and second manipulations includes at least partially withdrawing the outer member relative to the wound opening.

In embodiments, the wound opening extends through the abdominal cavity and wherein moving the outer member through each of the first and second manipulations includes advancing the first and second suture segments through at least fascia tissue surrounding the abdominal cavity.

In another embodiment, a surgical closure apparatus for facilitating closure of a wound includes a needle holder having an elongated holder member defining a longitudinal axis, a needle assembly having a needle shaft secured to the holder member of the needle holder and a suture needle extending from the needle shaft, and a needle protector. The needle protector includes a protector housing dimensioned for at least partial reception of the needle holder. The protector housing is configured for reciprocal longitudinal movement relative to the needle holder between an unarmed condition where a needlepoint of the suture needle is disposed within the protector housing and an armed condition where the needlepoint of the suture needle is exposed from the protector housing and positioned for passage through tissue adjacent a wound opening.

In embodiments, the protector housing of the needle protector defines a first opening for passage of at least one of the needle holder or needle shaft and a second opening for passage of at least the needlepoint of the suture needle. In some embodiments, the protector housing includes a tapered entry end segment and wherein the first opening is lateral of the entry end segment and the second opening extends through the entry end segment.

The surgical closure apparatus and method of use provides an effective and safe approach for closing a wound opening in tissue, particularly, within the abdominal cavity. The movement of the needle assembly between the unarmed and armed conditions of the suture needle is directly controlled by the clinician with direct confirmation of the respective condition of the suture needle being provided, in some embodiments, by the orientation of the manual actuator relative, e.g., to the first and second stops of the housing, or in other embodiments, by the location of the needle protector relative to the needle holder or the suture needle. Furthermore, the incorporation of the needle assembly within the apparatus removes the necessity of introducing needles through an access port to suture the surrounding wound, which is a highly skill dependent surgical task and may introduce additional trauma and associated recovery time.

Other advantages of the present disclosure will be appreciated from the following description.

BRIEF DESCRIPTION OF THE DRAWING(S)

Embodiments of the present disclosure will be appreciated by reference to the accompanying drawings wherein:

FIG. 1 is a perspective view of the surgical closure apparatus in accordance with the principles of the present disclosure illustrating the outer member, the needle assembly at least partially disposed within the outer member and the suture coupled to the needle assembly;

FIG. 2 is an exploded perspective view of the surgical closure apparatus;

FIG. 2A is an enlarged perspective view illustrating the suture needle of the needle assembly;

FIG. 14 is a side plan view of another embodiment of the surgical closure apparatus illustrating the needle holder, the needle protector slidably mounted relative to the needle holder and the needle assembly at least partially mounted within the needle holder with the needle in an unarmed condition;

FIG. 15 is a side cross-sectional view of the surgical closure apparatus of FIG. 14 further illustrating the needle assembly in the unarmed condition;

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

Figure 3:
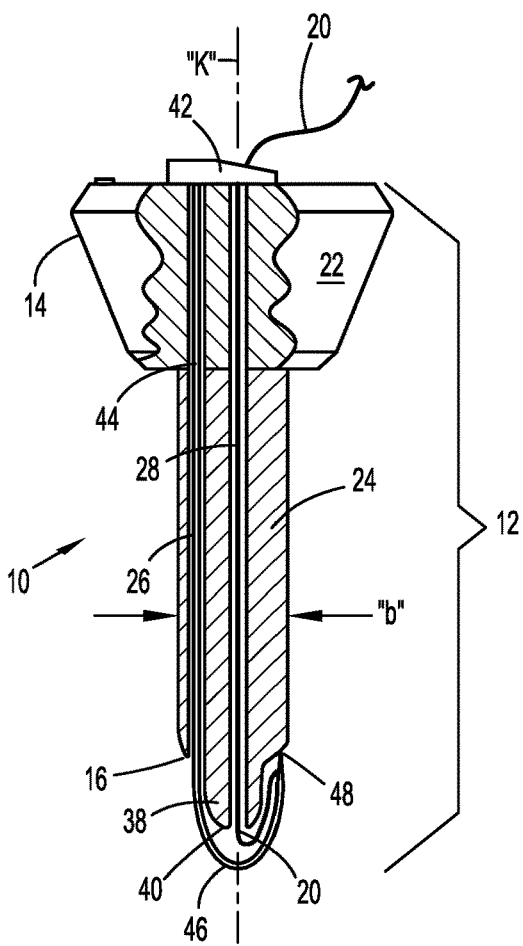
FIG. 3 is a side cross-sectional view of the surgical closure apparatus illustrating the arrangement of the needle assembly in an unarmed condition of the suture needle.

Referring now to the drawings where like reference numerals indicate similar components throughout the several views, FIGS. 1-3 illustrate a surgical closure apparatus 10 in accordance with an exemplary embodiment of the present disclosure. The surgical closure apparatus 10 is adapted to facilitate the closure of a wound opening in tissue, and, has particular application in the closure of a puncture or port wound created within the abdomen, e.g., through the abdominal wall, in connection with a laparoscopic surgical procedure. However, the surgical closure apparatus 10 and associated method of use also may be used to close a wound opening in other areas of the subject's body whether created during a surgical procedure or resulting from accident or trauma.

The surgical closure apparatus 10 includes an outer member 12 defining proximal and distal end portions 14, 16, a needle assembly 18 at least partially positionable within the outer member 12 and a suture 20 coupled to the needle assembly 18. The outer member 12 includes a housing 22 adjacent the proximal end portion 14 and an elongate member 24 extending distally from the housing 22. The housing 22 and the elongate member 24 may be monolithically formed, or alternatively, separate components secured to each other via conventional means. The outer member 12 defines a central longitudinal axis "k", and has first and second longitudinal passages 26, 28 extending at least partially through the housing 22 and the elongate member 24 as best depicted in FIG. 3. The first longitudinal passage 26 is radially spaced relative to the central longitudinal axis "k" and the second longitudinal passage 28 is in general longitudinal alignment with the central longitudinal axis "k". Other arrangements are also envisioned. The outer member 12, including the housing 22 and the elongate member 24, may be solid, in whole or in part, with the exception of the first and second longitudinal passages 26, 28, or alternatively, may be hollow and include internal tubes which define the first and second longitudinal passages 26, 28.

With reference again to FIGS. 1 and 2, the housing 22 includes a flared entry opening 30 in its proximal housing end face 32 in communication with the second longitudinal passage 28 for reception and passage of the suture 20. The housing end face 32 also includes a first stop 34 positioned between the central longitudinal axis "k" and the periphery of the housing 22, and a second stop 36 adjacent the periphery of the housing 22 in general diametrical opposed relation to the first stop 34. The first and second stops 34, 36 may be in the form of shelves or protrusions extending from the housing end face 32. The respective functions of the first and second stops 34, 36 will be discussed in greater detail hereinbelow.

Referring again to FIGS. 1-3, the elongate member 24 of the outer member 12 is generally cylindrical along a majority of its length and possesses a tapered end segment 38 adjacent the distal end portion 16 dimensioned to facilitate passage through tissue. The tapered end segment 38 defines a curved leading or distal-most surface 40 which is atraumatic to tissue to thereby minimize tissue snag or undesired piercing of the tissue as the outer member 12 passes through the wound opening. As shown, the second longitudinal passage 28 extends through the tapered segment 38 along the central longitudinal axis "k" while the first longitudinal passage 26 terminates proximal of the tapered segment 38.

The needle assembly 18 includes a manual actuator 42, an elongated needle drive 44 extending from the manual actuator 42 and a suture needle 46 connected to the needle drive 44. The manual actuator 42 is mounted for rotational movement relative to the housing 22 and is dimensioned for manual engagement by the clinician. The needle drive 44 is connected to the manual actuator 42 via conventional means and is at least partially disposed within the first longitudinal passage 26 of the outer member 12. The suture needle 46 is a curved needle, e.g., generally J-shaped, which leads to a needlepoint 48. In the alternative, the suture needle 46 may be linear and offset relative to the longitudinal axis "k" such that the needlepoint 48 extends toward the housing, e.g., generally V-shaped. The suture needle 46 may be monolithically formed with the needle drive 44 or a separate component secured to the needle drive 44 through conventional means. The suture needle 46 is at least partially disposed distal of or beyond the distal end portion 16 of the outer member 12. The suture needle 46 may include an eye 50 extending through the body of the needle 44 for passage of the suture 20 (FIG. 2A).

With continued reference to FIGS. 1-3, the suture 20 extends through the eye 50 of the suture needle 46 and through the second longitudinal passage 28 of the outer member 12 and external of the housing 22. In one embodiment, the suture 20 is not secured relative to the suture needle 46 and passes through the eye 50. In an alternative embodiment, the suture 20 may be secured relative to the eye 50. The suture 20 is capable of advancing or sliding through the second longitudinal passage 28 during use of the apparatus 10 in closing the wound opening. Suitable materials of fabrication for the suture 20 include natural or synthetic degradable materials, non-degradable materials, or combinations thereof.

Figure 4:
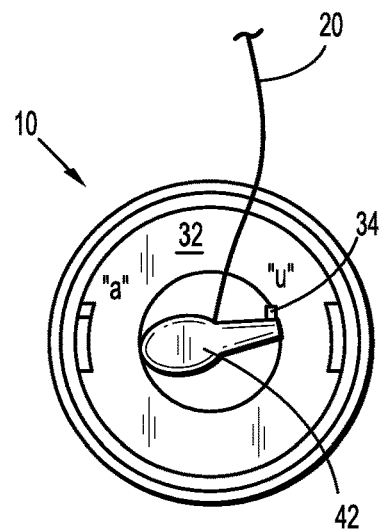
FIG. 4 is a top axial view of the surgical closure apparatus illustrating the positioning of the manual actuator of the needle assembly when in the unarmed condition of the suture needle.
Figure 5:
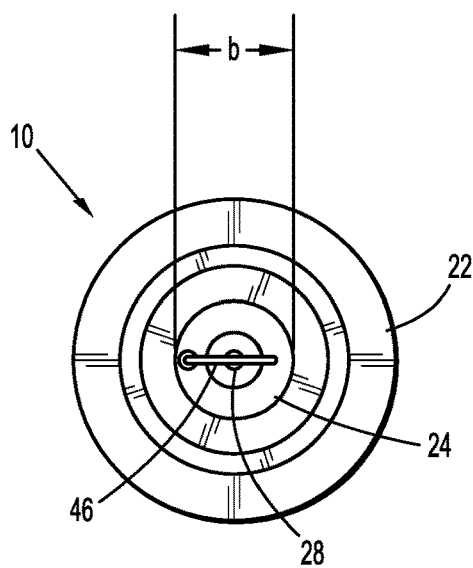
FIG. 5 is a bottom axial view of the surgical closure apparatus illustrating positioning of the suture needle of the needle assembly when in the unarmed condition.

The suture needle 46 of the needle assembly 18 is adapted to transition between an unarmed condition to facilitate insertion and passage of the apparatus 10 through the wound opening and an armed condition where the suture needle 46 is positioned to engage the tissue surrounding the wound opening. FIGS. 3-5 illustrate the unarmed condition of the suture needle 46 of the needle assembly 18. In the unarmed condition, the manual actuator 42 is directed radially inwardly relative to the central longitudinal axis "k" to a first position in contact with the first stop 34. Contact of the manual actuator 42 with the first stop 34 provides visual confirmation to the clinician that the suture needle 46 is in the unarmed condition. In embodiments, visual indicia such as an imprinted "u", representing "unarmed", may be disposed on the housing end face 32 to provide further confirmation of the unarmed condition of the suture needle 46. The first stop 34 will also prevent any further rotation of the manual actuator 42 in a counter-clockwise direction (FIG. 4) thereby preventing corresponding rotation of the needle drive 44 and the suture needle 46 toward an armed orientation. In addition, the manual actuator 42 may be dimensioned to releasably engage the suture 20 exiting the flared entry opening 30 (FIG. 2) when in its first position to minimize and/or prevent movement of the suture 20 within the second longitudinal passage 28 thereby reducing the potential of suture entanglement upon itself or the other components of the apparatus 10.

In the unarmed condition, the suture needle 46 is disposed radially inward relative to the central longitudinal axis "k" such that the needle 44 and the needlepoint 48 are at least partially or entirely confined within the outer boundary or diameter "b" defined by the elongate member 24 of the outer member 12. (FIG. 5) The curved shape of the suture needle 46 may also follow the contour defined by the leading surface 40 of the tapered end segment 38 thereby providing a reduced profile of the leading end of the apparatus 10 during insertion within the wound opening and maintaining the suture needle 46 in an approximated relation to the outer member 12 which minimizes inadvertent engagement of the suture needle 46 with the tissue surrounding the wound opening.

Figure 6:
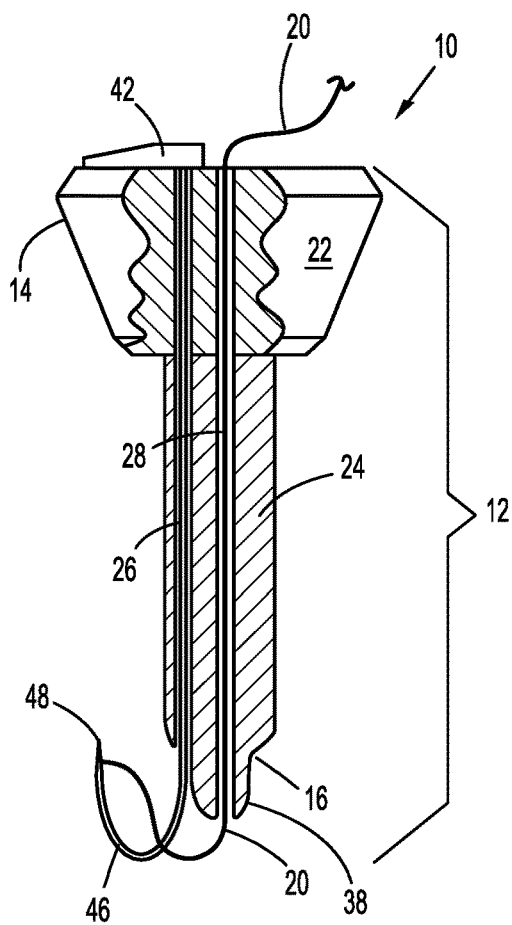
FIG. 6 is a side cross-sectional view of the surgical closure apparatus illustrating the arrangement of the needle assembly when in an armed condition of the suture needle.
Figure 7:
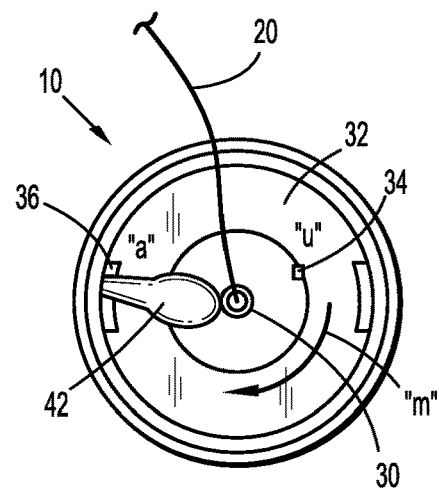
FIG. 7 is a top axial view of the surgical closure apparatus illustrating the positioning of the manual actuator of the needle assembly when in the armed condition of the suture needle.
Figure 8:
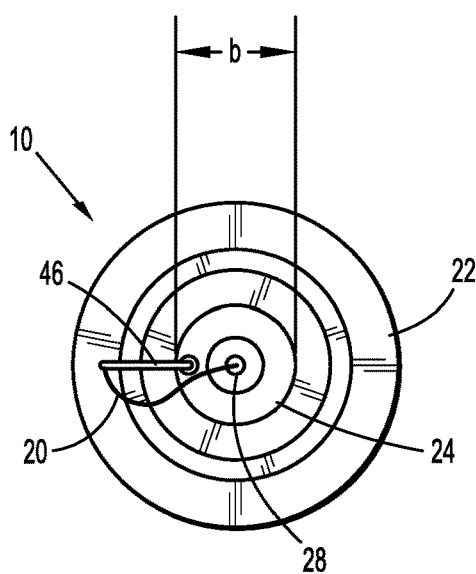
FIG. 8 is a bottom axial view of the surgical closure apparatus illustrating positioning of the suture needle of the needle assembly when in the armed condition.

FIGS. 6-8 illustrate the suture needle 46 of the needle assembly 18 in the armed condition. The armed condition is effected by rotating the manual actuator 42 in the direction "m" which causes corresponding rotation of the needle drive 44 and the suture needle 46. Upon achieving the armed condition, the manual actuator 42 engages the second stop 36 which provides confirmation, e.g., both tactile and visual, to the clinician that the suture needle 46 is armed. In embodiments, the housing end face 32 may have a printed "a", (representing "armed") next to the second stop 36 to also identify the armed condition of the suture needle 46. At least a major portion of the suture needle 46 and the needlepoint 48 are radially disposed beyond the boundary "b" of the elongate member 24 of the outer member 12 when in the armed condition positioned to pierce through tissue surrounding the wound opening.

FIGS. 9A-9G illustrate a method of use of the apparatus 10 in closing a wound opening. The following discussion will focus on the use of the apparatus 10 in closing a puncture wound created by an obturator or trocar during a laparoscopic procedure. However, it is envisioned that the apparatus 10 may have application in closure of wounds due to trauma in any area of the body.

Subsequent to the performance of a laparoscopic procedure or maneuver within the abdominal cavity, the attention of the clinician is directed to closing the puncture or port wound extending through the abdominal cavity. The clinician grasps the apparatus 10 and threads the suture 20 through the entry opening 30 of the housing end face 32 and through the second longitudinal passage 28. The suture 20 is then passed through the eye 50 of the suture needle 46 (FIG. 2A). In one method, the suture 20 is not secured relative to the eye 50. The suture needle 46 of the needle assembly 18 is placed in the unarmed condition of FIG. 9A by rotating the manual actuator 42 in the direction of directional arrow "j" such that the manual actuator 42 contacts the first stop 34 (FIG. 4). In the unarmed condition, the apparatus 10 is then introduced or positioned within the wound opening "w" extending through the subcutaneous tissue "s", fascia "f" and abdominal lining "l" of the abdominal wall. The apparatus 10 is advanced such that at least the suture needle 46 enters the underlying abdominal cavity "c". As indicted above, the tapered end segment 38, the rounded leading surface 40 of the tapered end segment 38 and the low profile provided by the orientation and relationship of the suture needle 46 with the rounded leading surface 40 facilitates passage through the wound opening "w" while minimizing inadvertent engagement with the surrounding tissue.

Figure 9A:
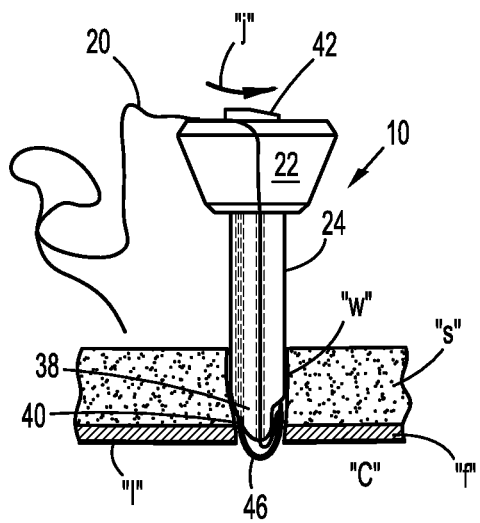
FIGS. 9A-9G illustrate a sequence of use of the surgical closure apparatus in closing a wound opening within the abdomen.
Figure 9B:
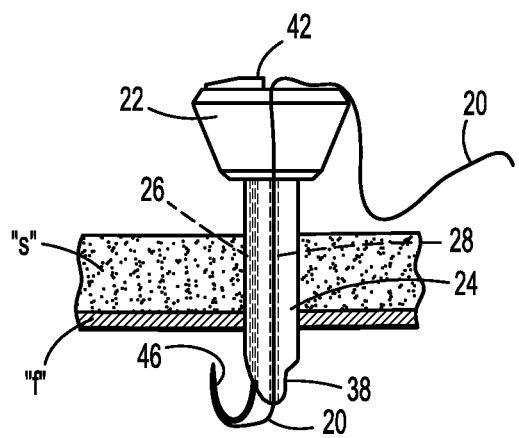
Figure 9C:
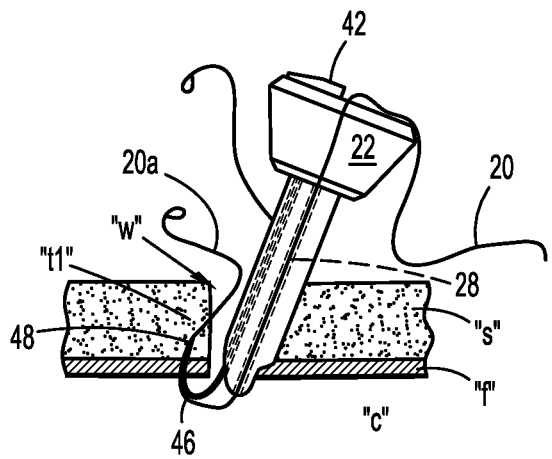
Figure 9D:
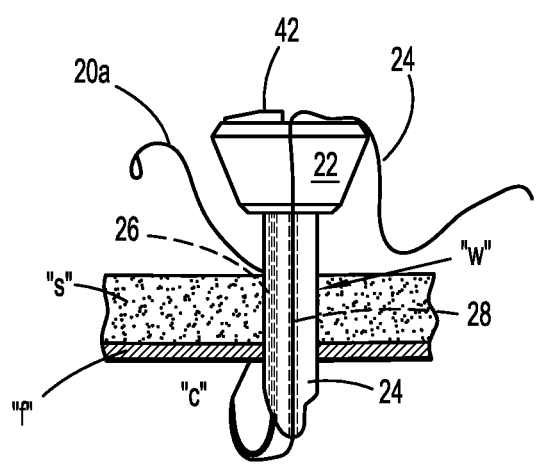

Once the suture needle 46 is disposed within the abdominal cavity "c", the suture needle 46 is moved to the armed condition through maneuvering of the manual actuator 42, e.g., via rotation of the manual actuator 42 to the second position (FIG. 7) against the second stop 36, as depicted in FIG. 9B. In the armed condition, the needlepoint 48 and at least a portion of the suture needle 46 is disposed outwardly of the elongate member 24 of the outer member 12 with the suture 20 coupled to the eye 50 of the suture needle 46 and extending back through the second longitudinal passage 28. Thereafter, the apparatus 10 is at least partially withdrawn relative to the wound opening "w", e.g., pulled in a proximal direction toward the clinician through a first manipulation, which causes the needlepoint 48 and the suture needle 46 to pierce through first tissue portions "t1", including fascia and/or subcutaneous tissue, surrounding the wound opening "w" to thereby pass a first suture segment 20a of the suture 20 through the first tissue portions "t1", as depicted in FIG. 9C. The apparatus 10 is retracted a sufficient distance to expose the first suture segment 20a of the suture 20 to the clinician. The first suture segment 20a may be grasped with, e.g., forceps, to pull the first suture segment 20a through the eye 50 of the needle 46 and through the first tissue portions "t1" outwardly of the abdominal cavity "c". During this movement of the first suture segment 20a, the suture 20 advances or slides through the second longitudinal passage 28 of the outer member 12. The apparatus 10 is then advanced back within the wound opening "w" while the first suture segment 20a is retained or secured external of the abdominal cavity "c" as depicted in FIG. 9D. As the apparatus 10 is advanced within the wound opening "w", the suture 20 slides within the second longitudinal passage 28 of the outer member 12.

Figure 9E:
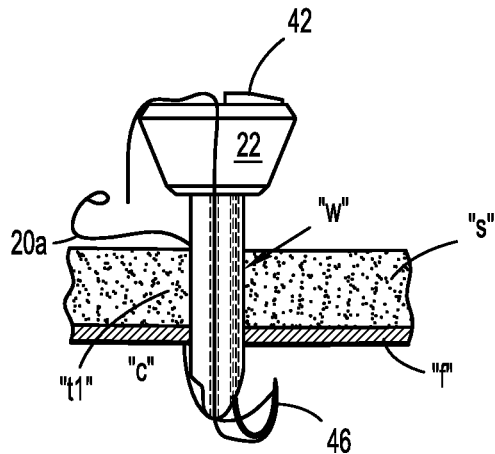
Figure 9F:
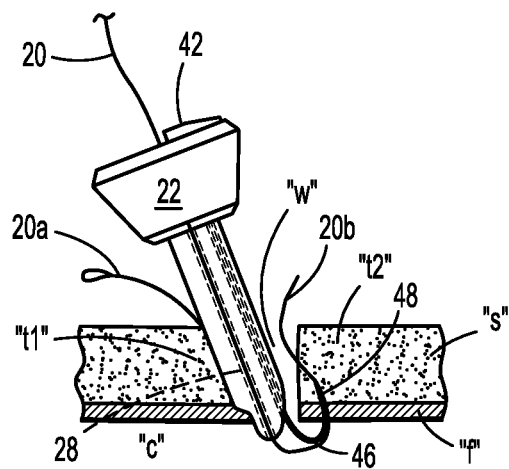
Figure 9G:
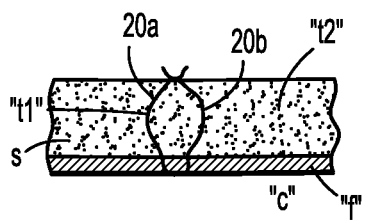

Referring now to FIG. 9E, the entire apparatus 10 is rearranged or rotated within the wound opening "w" through an arc segment of, e.g., 180° to position the suture needle 46 adjacent the opposed tissue on the other side of the wound opening "w". The apparatus 10 is again at least partially withdrawn relative to the wound opening "w" or pulled proximally toward the clinician through a second manipulation as depicted in FIG. 9F which causes the needlepoint 48 and attached suture 20 to pass through the second tissue portions "t2" surrounding the wound opening "w", including fascia "f" and/or the subcutaneous tissue "s", to expose the second suture segment 20b of the suture 20 from the abdominal cavity "c". During this movement, the suture 20 slides through the second longitudinal passage 28 of the outer member 12 in a similar manner as discussed hereinabove. With the first and second suture segments 20a, 20b exposed from the abdominal cavity "c" and passing through respective first and second tissue portions "t1", "t2" surrounding the wound opening "w", the suture 20 is removed from the apparatus 10 by pulling on the second suture segment 20b with forceps such that the remaining suture length slides distally through the second longitudinal passage 28 and out the tapered end segment 38. With the suture 20 released from the apparatus 10, the suture needle 46 is moved to the unarmed condition through manipulation of the manual actuator 42, e.g., via rotation of the manual actuator 42 to the first position (FIG. 4) against the first stop 34. The apparatus 10 is then removed from the wound opening "w". The first and second suture segments 20a, 20b of the suture 20 are tightened relative to the wound opening "w" and tied off in a conventional manner to close the wound opening "w" as shown in FIG. 9G.

Figure 10:
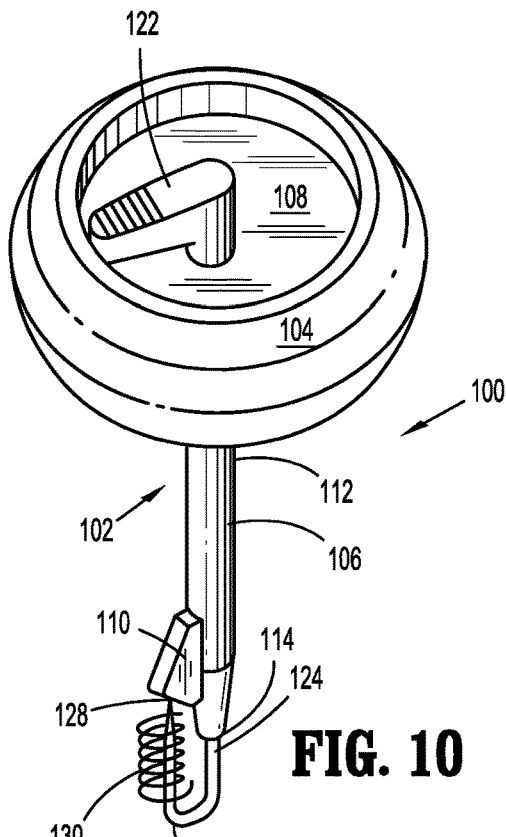
FIG. 10 is a perspective view of another embodiment of the surgical closure apparatus illustrating the outer member with the protective ledge, the needle assembly and the suture looped about the needle of the needle assembly.
Figure 11:
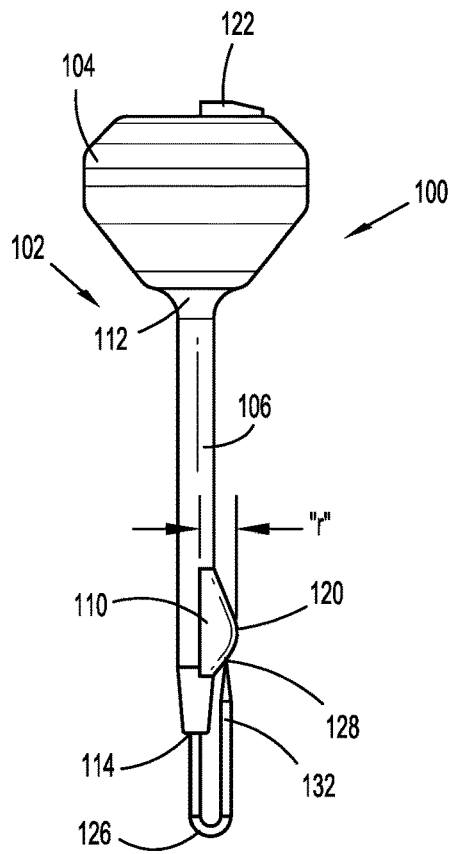
FIG. 11 is a side elevation view of the surgical closure apparatus of FIG. 10 in an unarmed condition of the needle assembly with the suture removed.

FIGS. 10-13 illustrate an alternate embodiment of the surgical closure apparatus. The surgical closure apparatus 100 includes some of the features described in connection with the embodiment of FIGS. 1-8. The closure apparatus 100 includes an outer member 102 having a housing 104 and an elongate member 106 depending from the housing 104. The housing defines an internal annular recess 108. The elongate member 106 includes a protective ledge 110 intermediate the proximal and distal ends 112, 114 of the elongate member 106 and extending radially outwardly from the wall of the elongate member 106. The protective ledge 110 defines a leading edge surface 116 and a trailing edge surface 118 which are respectively tapered at opposite, e.g., oblique, angles of inclination "α1", "α2" with respect to the longitudinal axis "p" of the outer member 102. (FIG. 13) The angles of inclination "α1", "α2" are selected to facilitate advancement and withdrawal of the elongate member 106 within the wound opening, and may range between about 5° to about 45°. The leading and trailing edge surfaces 116, 118 are interconnected by an atraumatic or curved surface 120 which will minimize trauma to tissue as the apparatus 100 is manipulated within the wound opening. The protective ledge 110 defines an outer boundary "r" defined between the wall of the elongate member 106 and the curved surface 120 (FIG. 11).

The needle assembly is substantially similar to the needle assembly described in connection with the embodiment of FIGS. 1-8 and includes a manual actuator 122, a needle drive 124 extending from the manual actuator 122 and a curved suture needle 126. The suture needle 126 is manipulable between the unarmed condition of FIG. 11 and the armed condition of FIG. 12 through rotation of the manual actuator 122 which resides within the annular recess 108 in the housing 104. In the unarmed condition of FIG. 11, the suture needle 126 is aligned with the protective ledge 110 and thereby confined within the outer boundary "r", e.g., the needlepoint 128 and the suture needle 126 are radial inward of the outer boundary "r" of the protective ledge 110. In the armed condition, the needlepoint 128 of the suture needle 126 is disposed on the opposite side of the elongate member 106 displaced from the protective ledge 110 and in position to pierce through tissue.

Figure 12:
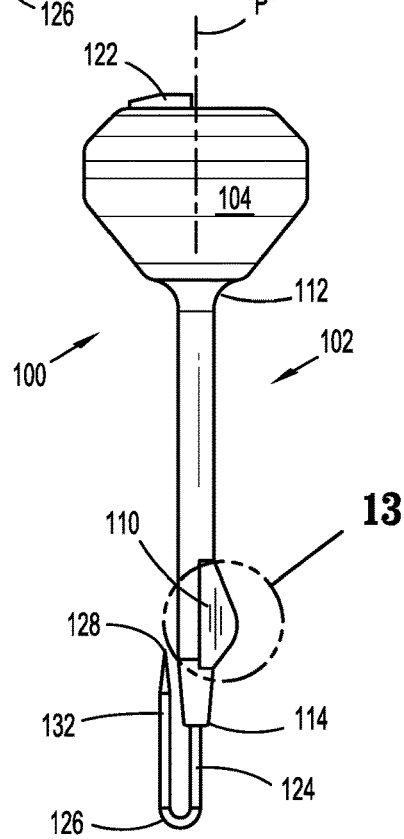
FIG. 12 is a side elevation view of the surgical closure apparatus of FIG. 10 in an armed condition of the needle assembly with the suture removed.
Figure 13:
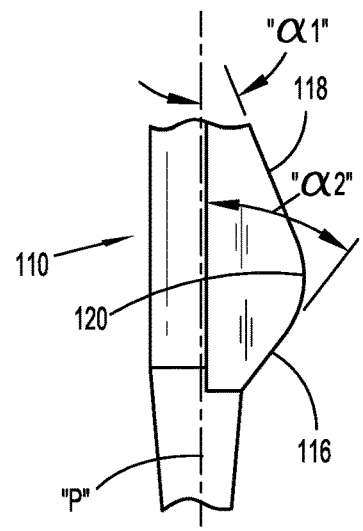
FIG. 13 is an enlarged isolated view of the area of detail identified in FIG. 12.

The suture 130 extends through an eye 132 in the suture needle 126 and is wrapped or coiled about the suture needle 126 as best depicted in FIG. 10. In FIGS. 11-12, the suture 130 is removed for illustrative purposes. The suture 130 does not extend back through a passageway within the elongate member 106 as described in the embodiment of FIGS. 1-8. Rather, the elongate member 106 is devoid of a passageway, and the length of suture 130 to be utilized in the wound closure procedure is wrapped or looped about the suture needle 126.

The use of the apparatus 100 is similar to the use of the apparatus 10 described in connection with FIGS. 9A-9G. With the suture needle 126 in the unarmed condition of FIG. 11, the apparatus 100 is advanced within the wound opening such that at least the suture needle 126 and possibly the protective ledge 110 are disposed within the abdominal cavity. During passage through tissue, the taper of the leading edge surface 116 of the protective ledge 110 will facilitate passage of the elongate member 106 within the wound opening. In addition, the needlepoint 128 and the needle 126 are confined within the boundary "r" of the protective ledge 110 to avoid undesired piercing of tissue surrounding the wound opening. Thereafter, the suture needle 126 is moved to the armed condition of FIG. 12, and the apparatus 100 is at least partially withdrawn within the wound opening whereby the suture needle 126 engages tissue, including fascia tissue, surrounding the wound opening. Upon exposure of the needlepoint 128 of the suture needle 126 from the tissue, an exposed end segment of the suture 130 is grasped with, e.g., graspers, and held by the clinician. During the at least partial withdrawal of the apparatus 100 within the wound, the trailing edge surface 118 of the protective ledge 110, due to its angular orientation, will facilitate passage of the elongate member 106 in this direction. The apparatus 100 is reintroduced or advanced back within the wound opening while the exposed suture end segment is held by the clinician whereby a remaining segment of the suture 130 slides through the eye 132 of the suture needle 126. The apparatus 100 is rotated within the wound opening through an arc segment of, e.g., 180°, to position the suture needle 126 adjacent the opposed tissue on the other side of the wound opening. The apparatus 100 is again at least partially withdrawn relative to the wound opening causing the needlepoint 128 and attached suture 130 to pass through the opposed tissue portions, including fascia tissue, surrounding the wound opening. The clinician grasps the exposed segment of the suture 130. With the two suture segments exposed from the abdominal cavity and passing through respective opposed tissue portions surrounding the wound opening, the remaining suture is pulled through the eye 132 of the suture needle 126 to release the entire length of suture 130 from the apparatus 100. With the suture 130 released from the apparatus 100, the suture needle 126 is moved to the unarmed condition through manipulation of the manual actuator 120 and the apparatus 100 is then removed from the wound opening. The suture segments of the suture 130 are tightened relative to the wound opening and tied off to close the wound opening.

FIGS. 14-15 illustrate an alternate embodiment of the surgical closure apparatus. The closure apparatus 200 includes a needle holder 202, a needle assembly 204 mounted to the needle holder 202 and a needle protector 206 slidably mounted relative to the needle holder 202. The needle holder 202 includes a T-shaped handle 208 and an elongated holder member 210 depending from the handle 208 and defining a longitudinal axis "w". The needle assembly 204 includes a needle shaft 212 and a curved suture needle 214 extending from the needle shaft 212. The needle shaft 212 is secured within the holder member 210 of the needle holder 202 through conventional methodologies. The suture needle 214 may include an opening or eye (not shown) for engaging a suture. The needle holder 202 and the needle assembly 204 each may be monolithically formed as a single unit.

The needle protector 206 includes a protector housing 216 defining a longitudinal passage 218 for reception of the needle holder 202 and, possibly, the needle shaft 212. The longitudinal passage 218 may be defined, in part, by an internal tube extending through the protector housing 216. The protector housing 216 has a tapered and/or arcuate entry end segment 220 positioned adjacent the suture needle 214 and being configured to facilitate passage through the wound opening. The protector housing 216 further defines a first opening 222 adjacent, e.g., lateral of, the entry end segment 220 in longitudinal alignment with the longitudinal passage 218 and a second opening 224 within the entry end segment 220. The first opening 222 is dimensioned to permit reciprocal movement of the holder member 210 of the needle holder 202 and the needle shaft 212 of the needle assembly 204. The second opening 224 receives at least the needlepoint 226 of the suture needle 214 when in the unarmed condition of the needle assembly 204 depicted in FIGS. 14-15. The remainder of the entry end segment 220 is closed to assist in penetrating through the wound opening and/or tissue. The protector housing 216 may further include a grip 228 in the form of, e.g., serrations, ribs, irregularities on its outer surface to facilitate grasping engagement by the clinician.

Figure 16:
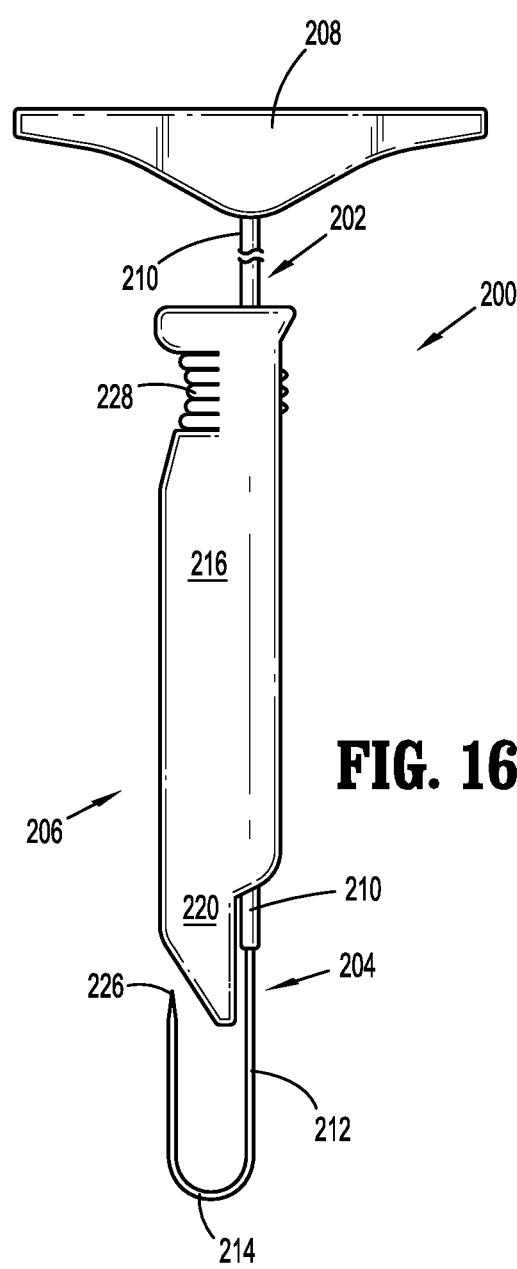
FIG. 16 is a side plan view of the surgical closure apparatus of FIG. 14 illustrating the needle assembly in the armed condition.
Figure 17:
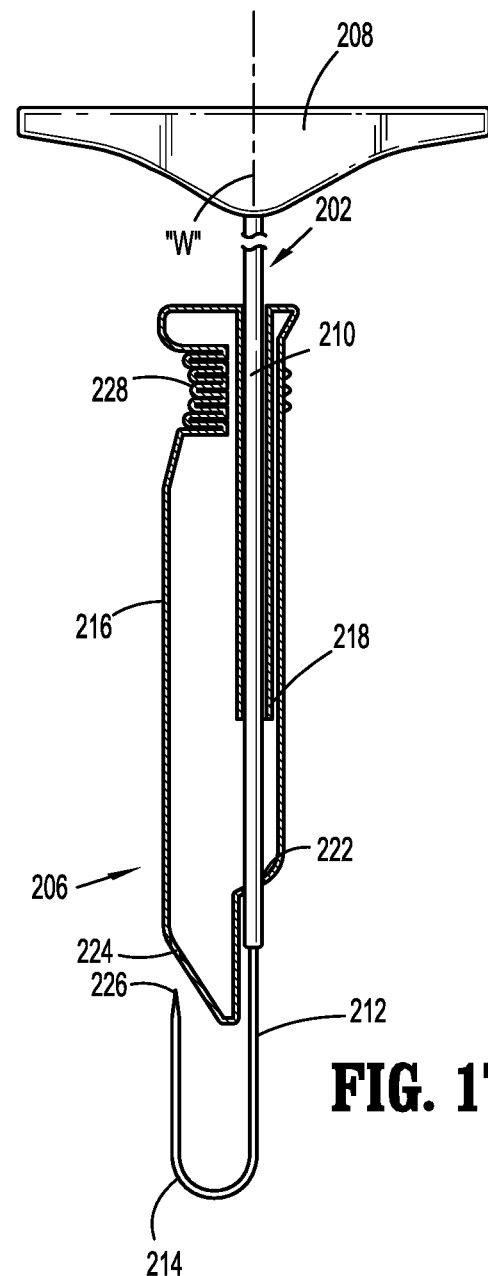
FIG. 17 is a side cross-sectional view of the surgical closure apparatus of FIG. 14 further illustrating the needle in the armed condition.

The needle protector 206, including the protector housing 216, is adapted for reciprocal longitudinal movement relative to the needle holder 202 and the needle assembly 204 between the unarmed condition of FIGS. 14-15 and the armed condition of FIGS. 16-17 through relative sliding movement of the needle holder 202 within the longitudinal passage 218 of the protector housing 216. When in the unarmed condition of FIGS. 14-15, the needle shaft 212 is confined within the outer boundary of the protector housing 216 and the needlepoint 226 of the suture needle 214 is received within the second opening 224 of the protector housing 216. In particular, the needle shaft 212 is accommodated within the open space 230 created by the tapered configuration of the entry end segment 220 while the suture needle 214 generally follows the outer surface or contour of the entry end segment 220. This arrangement significantly reduces the profile of the closure apparatus 200 thereby facilitating entry and passage within the wound opening. In the armed condition of FIGS. 16-17, the needlepoint 226 and the suture needle 214 are exposed from the protector housing 216 positioned to engage tissue portions surrounding the wound opening.

The use of the closure apparatus 200 is similar to the use of the apparatuses 10, 100 described hereinabove. With the needle assembly 204 in the unarmed condition of FIGS. 14-15, the closure apparatus 200 is advanced, by engagement of the handle 208, within the wound opening to position the suture needle 214 within the abdominal cavity. The needle protector 206 is slid or retracted toward the handle 208 to the armed condition of FIGS. 16-17 to expose the suture needle 214 and the needlepoint 226 for use in passing the suture (not shown) through tissue margins surrounding the wound opening. The closure apparatus 200 may be rotated and at least partially withdrawn relative to the wound opening as needed to effect closure of the wound opening. Confirmation of the unarmed or armed condition of the needle assembly 204 may be ascertained by viewing the position of the needle protector relative to the needle holder 202, e.g., the handle 208 of the needle holder 202.

Although the above-described method of wound closure includes passing two segments through tissue surrounding the wound opening to close the wound, it is envisioned that more than two suture segments may be utilized. For example, four suture segments may be applied around the wound opening, which would entail, e.g., rotating the apparatuses 10, 100, 200 through an arc sector of approximately 90° within the wound opening subsequent to application of each suture segment.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A surgical closure apparatus for facilitating closure of a wound, comprising:

an outer member dimensioned for positioning within a wound opening and defining a central longitudinal axis, the outer member having a first longitudinal passage and a second longitudinal passage;

a needle assembly including a needle drive at least partially disposed within the first longitudinal passage of the outer member and a suture needle fixedly mounted to the needle drive, the needle drive defining a longitudinal axis, the suture needle adapted for rotational movement about the longitudinal axis of the needle drive relative to the central longitudinal axis between an unarmed condition and an armed condition through manipulation of the needle drive, the suture needle positioned for passage through the tissue adjacent the wound opening when in the armed condition; and a suture configured for at least partially closing the wound opening within the tissue, the suture coupled to the suture needle and at least partially extending through the second longitudinal passage of the outer member.

2. The surgical closure apparatus according to claim 1 wherein the suture needle is curved and defines a needlepoint.

3. The surgical closure apparatus according to claim 2 wherein at least the needlepoint of the suture needle is disposed radial outwardly relative to the outer member when in the armed condition of the suture needle.

4. The surgical closure apparatus according to claim 3 wherein at least the needlepoint of the suture needle is disposed radial inwardly relative to the outer member when in the unarmed condition of the suture needle.

5. The surgical closure apparatus according to claim 4 wherein the needle drive is rotatable within the first longitudinal passage of the outer member to cause corresponding rotational movement of the suture needle between the unarmed condition and the armed condition.

6. The surgical closure apparatus according to claim 5 wherein the needle assembly includes a manual actuator coupled to the needle drive, the manual actuator movable to cause corresponding rotational movement of the needle drive and the suture needle between the unarmed condition and the armed condition.

7. The surgical closure apparatus according to claim 6 wherein the outer member includes a housing and an elongate member extending from the housing, the manual actuator mounted to the housing for rotational movement between a first position corresponding to the unarmed condition of the suture needle and a second position corresponding to the armed condition of the suture needle.

8. The surgical closure apparatus according to claim 7 wherein the housing includes a first stop for engaging the manual actuator at the first position and a second stop for engaging the actuator at the second position.

9. The surgical closure apparatus according to claim 1 wherein the outer member includes a tapered end segment configured to facilitate passage through the wound opening.

* * * * *